United States Patent
Ahari et al.

[11] Patent Number: 5,944,727
[45] Date of Patent: Aug. 31, 1999

[54] STENT/GRAFT CATHETER HANDLE

[75] Inventors: Frederick Ahari; Jody W. Stallings, both of Clearwater, Fla.; Richard C. Fortier, Concord; Bruce Adams, Malden, both of Mass.

[73] Assignee: Datascope Investment Corp., Montvale, N.J.

[21] Appl. No.: 09/145,405

[22] Filed: Sep. 2, 1998

[51] Int. Cl.⁶ .................................................. A61B 17/00
[52] U.S. Cl. ............................................. 606/108; 623/1
[58] Field of Search ............................... 606/1, 108, 154, 606/158, 200; 623/1, 12

[56] References Cited

U.S. PATENT DOCUMENTS 5,391,172  2/1995  Williams et al. .
5,697,948  12/1997 Marin et al. .
5,702,418  12/1997 Ravenscroft .
5,759,186  6/1998  Bachmann et al. ...................... 606/108
5,833,694  11/1998 Poncet ..................................... 606/108

OTHER PUBLICATIONS

Boston Scientific Marketing Brochure for Symphony Nitinol Stent Product, four pages, see handle on page four.

*Primary Examiner*—Michael Buiz
*Assistant Examiner*—William Lewis
*Attorney, Agent, or Firm*—Abraham P. Ronai

[57] ABSTRACT

A stent/graft catheter delivery handle comprising a housing and a trigger pivotally connected to the housing on one end of the trigger. Squeezing the free end of the trigger towards the handle housing shifts a pawl, which is engaged with grooves on the outer surface of a stent/graft delivery catheter, longitudinally along the length of the catheter. Shifting of the pawl has the effect of retracting the sheath of the catheter relative to the plunger (inner lumen assembly) of the catheter and thus deploying a stent/graft stored in a proximal end of the catheter.

10 Claims, 6 Drawing Sheets

STENT/GRAFT CATHETER HANDLE

BACKGROUND OF THE INVENTION

1. Field of the Invention

The invention relates to a stent/graft deployment catheter handle. More particularly, the invention relates to a stent/graft deployment catheter handle, incorporating a ratchet-like actuation mechanism, capable of deploying a stent/graft accurately.

2. Description of the Prior Art

An abdominal aortic aneurysm (AAA) is a sac caused by an abnormal dilatation of the wall of the aorta as it passes through the abdomen. The aorta is the main artery of the body, supplying blood to all organs and parts of the body except the lungs. It arises from the left ventricle of the heart, passes upward, bends over and passes down through the thorax and through the abdomen, and finally divides into the iliac arteries which supply blood to the pelvis and lower extremities.

The AAA ordinarily occurs in the portion of the aorta below the kidneys. When left untreated, the aneurysm will eventually cause the sac to rupture with ensuing fatal hemorrhaging in a very short time. The repair of abdominal aortic aneurysms has typically required major abdominal surgery in which the diseased and aneurysmal segment of the aorta is bridged with a prosthetic device, such as a synthetic graft.

As with all major surgeries, there are many disadvantages to the above mentioned surgical technique, the foremost of which is the high mortality and morbidity rate associated with surgical intervention of this magnitude. Other disadvantages of conventional surgical repair include the extensive recovery period associated with such surgery; difficulties in suturing the graft to the aorta; the unsuitability of the surgery for many patients, particularly older patients exhibiting comorbid conditions; and the problems associated with performing the surgical procedure on an emergency basis after the aneurysm has already ruptured.

In view of the above mentioned disadvantages of conventional surgical repair techniques, techniques have been developed for repairing AAAs by intraluminally delivering an aortic graft to the aneurysm site through the use of a catheter based delivery system, and securing the graft within the aorta using an expandable stent. Since the first documented clinical application of this technique was reported by Parodi et al. in the Annals of Vascular Surgery, Volume 5, pages 491–499 (1991), the technique has gained more widespread recognition and is being used more commonly. As vascular surgeons have become more experienced with this endovascular technique, however, certain problems have been encountered relating to deployment and accurate positioning of the aortic graft.

The catheter based delivery system generally comprises a sheath and a plunger slidingly disposed within said sheath. A compressed aortic stent/graft, which comprises a graft disposed about a stent, is disposed within the distal end (the end closer to the heart when inserted) of the sheath. Upon positioning of the catheter within the patient, the sheath is retracted relative to the plunger, thereby exposing the stent/graft and allowing it to self-expand or be mechanically expanded. If properly positioned, the proximal end of the deployed stent/graft should coincide with the position of the distal end of the plunger upon initial positioning of the catheter. Generally, the sheath is retracted relative to the plunger simply by manually pulling the sheath away from the patient while holding the plunger still. U.S. Pat. No. 5,702,418 discloses a sheath having a knob, on the outer surface of its proximal end, to facilitate the manual retraction of the sheath as described above. One major problem with such a manual deployment method is that while retracting the sheath the plunger may be inadvertently moved, upstream or downstream, thereby displacing the predetermined deployment site for the stent/graft. Since the ultimate position of the deployed stent/graft is determined by the position of the distal end of the plunger just before deployment, if the plunger is inadvertently moved, upstream or downstream, while retracting the sheath, the stent/graft may not be properly positioned, and therefore, may not properly bridge the aneurysm upon deployment. It is critical, therefore, that the plunger not be moved during deployment of the stent/graft, i.e. during retraction of the sheath.

Friction between the outer surface of the compressed stent/graft and the inner surface of the sheath often makes retraction of the sheath a bit difficult. This difficult retraction of the sheath leads to fidgeting of the plunger by the surgeon during deployment and amplifies the problem of maintaining the plunger still during deployment. U.S. Pat. Nos. 5,391,172 and 5,697,948 disclose stent delivery handles for providing relative motion between the sheath of a stent delivery catheter and an underlying catheter, i.e. a plunger. These handles basically comprise a tube to which the plunger is attached to and within which the sheath is slidingly disposed. Holding on to the handle, one can retract the sheath by pulling it towards the proximal end of the handle. Although these handles provide a better grip onto the plunger, they do not decrease the likelihood that the entire handle, and therefore the plunger, will be displaced while the sheath is being retracted.

Another hybrid of a handle, produced by MedTronics Corp. (Eden Prairie, Minn.), comprises a rack and pinion design. The sheath, having a plurality of ridges on its outer surface, is slidingly disposed within a lumen in a handle and serves as the rack. A pinion rotatably attached to the handle and extending into the lumen is capable of shifting the sheath, the rack, in one direction. The proximal end of the plunger is fixed in the handle. Upon positioning of the catheter in the patient, the pinion is rotated, thereby retracting the sheath, relative to the plunger, and deploying the stent/graft. Although this design reduces the likelihood that the plunger will be moved relative to the sheath it has a major drawback. A large pinion is required to achieve the necessary force to shift the sheath relative to the plunger and to ensure passage of the sheath through a potential obstruction in the vasculature of a patient. A large pinion is bulky, and therefore, difficult to handle. Another problem with a large pinion is that it must be rotated many revolutions to withdraw the sheath only a small distance.

SUMMARY OF THE INVENTION

Accordingly, it is an object of the invention to produce a handle which is capable of accurately deploying a stent/graft.

It is another object of the invention to produce a handle which minimizes the likelihood of handle movement during retraction of the sheath.

The invention is a stent/graft catheter delivery handle comprising a housing and a trigger pivotally connected to the housing on one end of the trigger. Squeezing the free end of the trigger towards the handle housing shifts a pawl, which is engaged with grooves on the outer surface of a stent/graft delivery catheter, longitudinally along the length of the catheter. Shifting of the pawl has the effect of retracting the sheath of the catheter relative to the plunger (inner lumen assembly) of the catheter and thus deploying a stent/graft stored in a distal end of the catheter.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
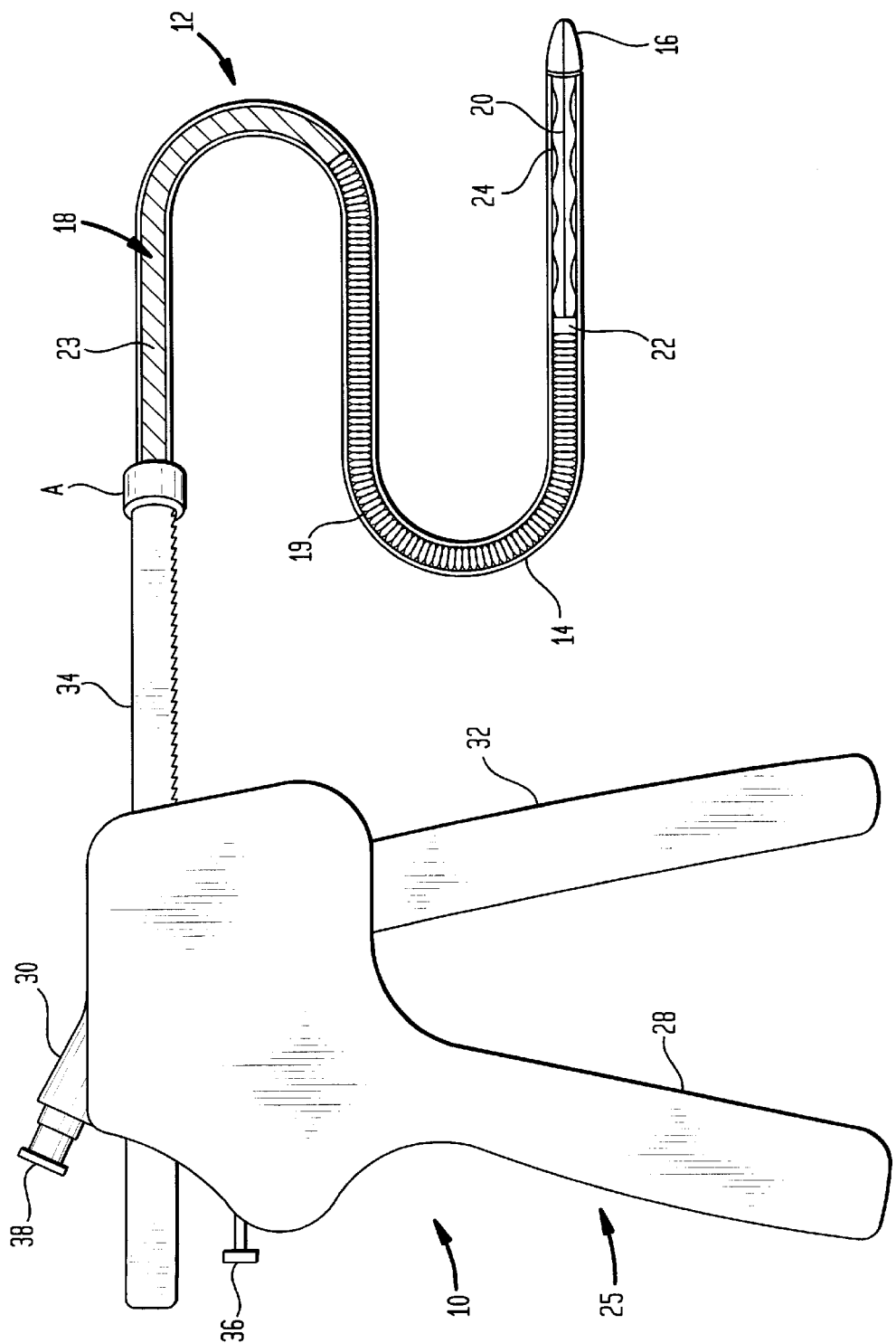
FIG. 1 is plan view of a stent/graft delivery system handle and a longitudinal cross section view of a stent/graft delivery catheter attached to said handle.

FIG. 1 illustrates a plan view of a stent/graft delivery system handle, generally designated 10, and a longitudinal cross section view of a stent/graft delivery catheter, generally designated 12, attached to said handle 10. The catheter 12 has proximal and distal ends and comprises a sheath 14, a tip 16, and a plunger 18, each having proximal and distal ends. Note that the further distal a portion of the catheter 12 is, the closer to the heart of a patient said catheter 12 is upon insertion. The tip 16 is the most distal portion of the catheter 12. The plunger 18 comprises an inner lumen tube 20, having proximal and distal ends, and a stent/graft stabilizer 22, having proximal and distal ends, attached proximal to the distal end of the inner lumen tube 20, and a spring 19 and semi-rigid tube 23 both disposed about the inner lumen tube 20. The distal end of the inner lumen tube 20 is attached to the tip 16. The inner lumen tube 20 and the stabilizer 22 are slidingly disposed within the sheath 14. A stent/graft 24 is disposed about the distal end of the inner lumen tube 20, between the stabilizer 22 and the tip 16, and is packed in a compressed state within the distal end of the sheath 14. Note that the invention may be used to deploy other deployable devices including, but not limited to, a self-expanding or mechanical stent with or without a graft.

The handle 10 comprises a housing 25, a trigger 32 having top and bottom ends, a ratchet tube 34 having proximal and distal ends, and a release button 36. A breakout 30, having a guidewire port 38, is attached to the housing 25. The housing 25 comprises two halves: a left housing 26 and a right housing 28 (see FIG. 3). The proximal end of the sheath 14 is attached to the distal end of the ratchet tube 34 at the point designated A. Upon insertion and proper positioning of the catheter 12 in a patient, the sheath 14 is retracted relative to the plunger 18, so as to allow the stent/graft 24 to deploy, by squeezing the trigger 32 and the housing 25 towards each other. The only forces applied to the handle 10 in order to retract the sheath 14 are opposing forces on the trigger 32 and the housing 25. These forces are generally directed in opposing directions, i.e. towards each other, and therefore, tend to cancel each other out. Furthermore, these opposing forces do not tend to result in any random forces on the handle 10 itself which might move the handle 10 relative to the patient's body, and thereby, result in a inaccurately deployed stent/graft 24.

Figure 2:
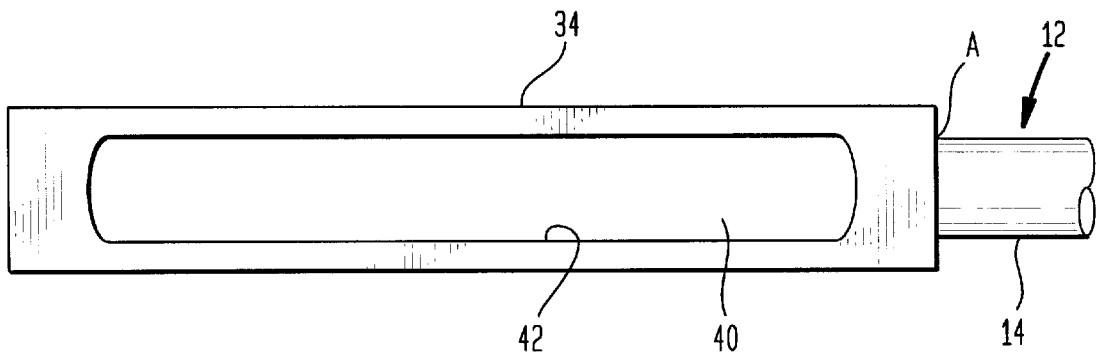
FIG. 2 is top plan view of the ratchet tube attached on its distal end to the sheath.

FIG. 2 illustrates a top view of the ratchet tube 34 attached on its distal end to the proximal end of the sheath 14. The point of attachment is designated A. A distal portion of the entire catheter 12 is cut off for clarity. The ratchet tube 34 comprises a ratchet tube lumen 40 and a ratchet tube slot 42. The ratchet tube slot 42 lies between the proximal and distal ends of the ratchet tube 34.

Figure 3:
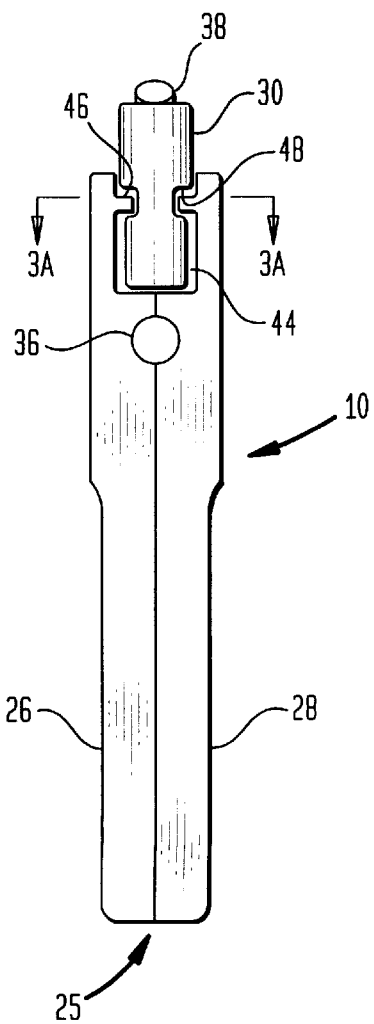
FIG. 3 illustrates a back view of the handle and the breakout.

FIG. 3 illustrates a back view of the handle 10. The left housing 26 and the right housing 28 are attached together. A breakout slot 44 exists on the top of the handle 10 between the left housing 26 and the right housing 28. The breakout slot 44 accommodates the breakout 30. The breakout 30 is secured in place partially by opposing first pins 46 which project into the breakout slot 44 and slide into slots 48 (seen also in FIG. 5) on opposing sides of the breakout 30.

Figure 4:
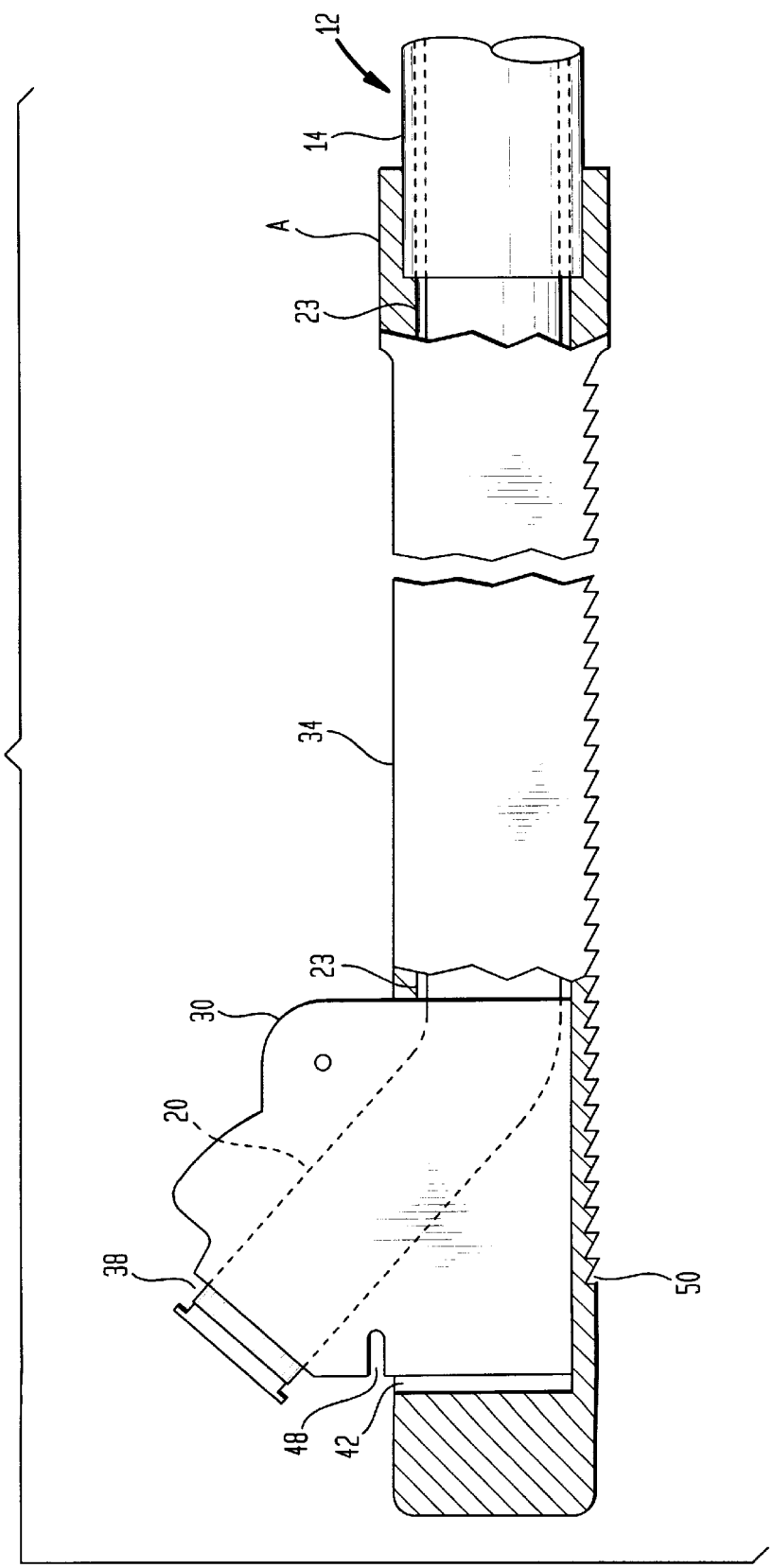
FIG. 4 illustrates an elevation view of the ratchet tube and the breakout attached to the catheter plunger.

FIG. 4 illustrates an elevation view of the ratchet tube 34 and the breakout 30. Portions of the ratchet tube 34 are peeled away so as to expose the proximal end of the sheath 14 and also to expose the breakout 30 which lies in the ratchet tube slot 42. The distal end of the ratchet tube 34 is disposed about and attached to the proximal end of the sheath 14 at point A. The proximal end of the inner lumen tube 20 is disposed within a breakout plunger lumen (not shown) and terminates at the guidewire port 38. The proximal end of the semi-rigid tube 23 is attached to the distal end of the breakout 30. The proximal portion of the inner lumen tube 20, which extends proximally beyond the proximal end of the semi-rigid tube 23 and which is disposed within the breakout 30, is shown as dotted lines. The breakout 30 and plunger 18 are slidable, relative to the ratchet tube 34 and the sheath 14, between the proximal and the distal ends of the ratchet tube slot 42. The ratchet tube 34 has saw teeth like grooves 50 on it outer surface positioned diametrically opposite to the ratchet tube slot 42. The grooves 50 are parallel and are found along a substantial portion of the length of the ratchet tube 34.

Figure 5:
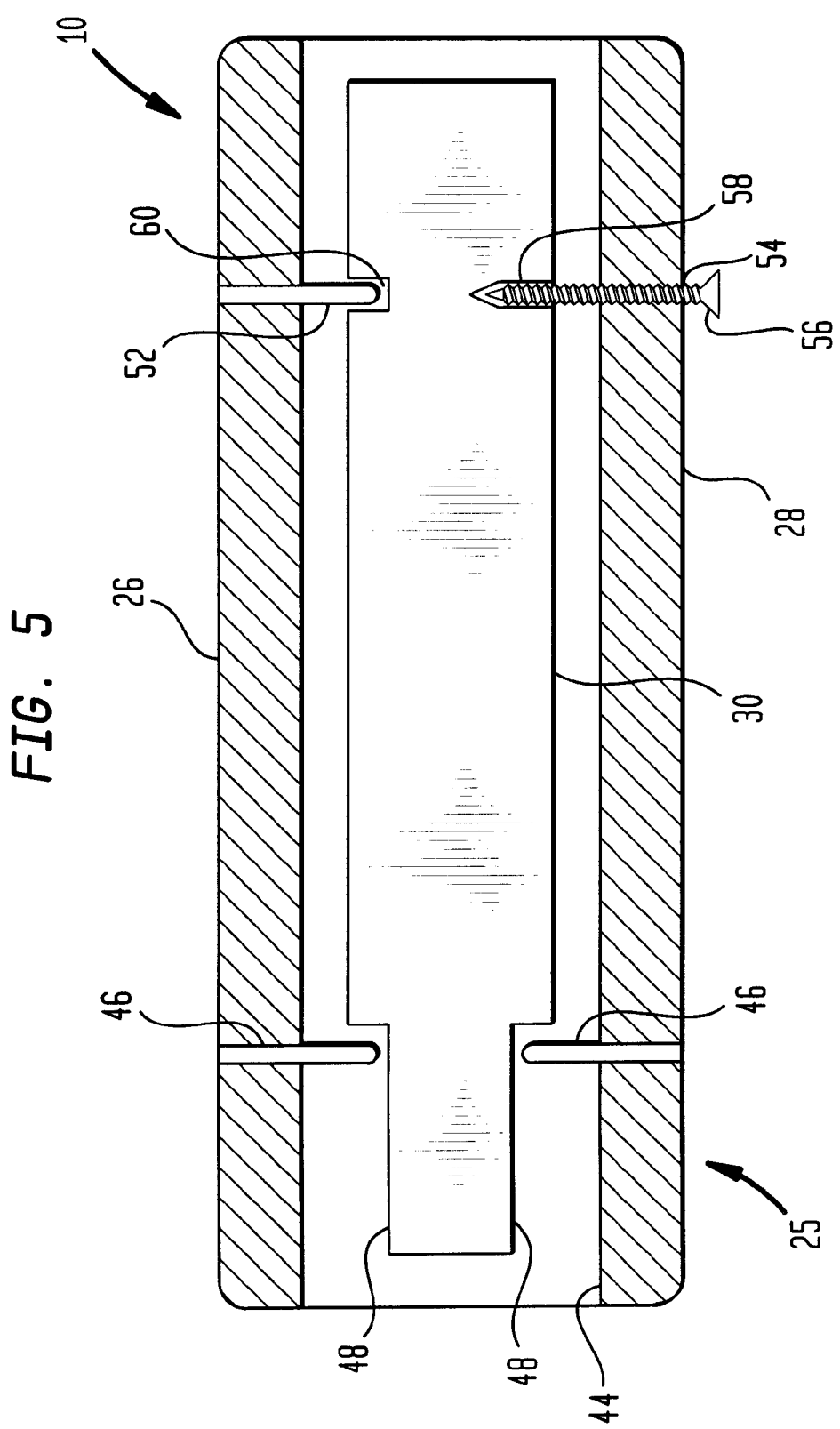
FIG. 5 is a longitudinal cross section of the handle, taken along lines 3A—3A in FIG. 3, illustrating how the breakout connects to the handle.

FIG. 5 is a longitudinal cross section of the handle 10 and the breakout 30, taken along lines 3A—3A in FIG. 3, illustrating how the breakout 30 is removably secured to the handle 10. The ratchet tube 34 is not shown for clarity. The opposing first pins 46 (also seen in FIG. 3) project into a proximal end of the breakout slot 44 and one second pin 52 projects into a distal end of the breakout slot 44. Directly opposite the second pin 52 is a first screw hole 54, in the right housing 28, and a second screw hole 58, in the breakout 30, which accommodate a securing screw 56 for locking the breakout 30 to the handle 10. The breakout 30 has two slots 48 (also seen in FIG. 3) on opposing sides on its proximal end and two opposing holes, the second screw hole 58 and a third hole 60, on its distal end. The breakout 30 is attached to the handle 10 by sliding it from right to left, such that the first pins 46 slide into the slots 48, and then shifting the breakout 30 towards the left housing 26 such that the second pin 52 fits into the third hole 60. Finally, the securing screw 56 is screwed into the first securing hole 54 and the second securing hole 58. The breakout 30 pin and hole arrangement allows a surgeon to easily and quickly removably attach the breakout 30, and thus the catheter 12, to the handle 10 with only one securing screw 56.

Figure 6:
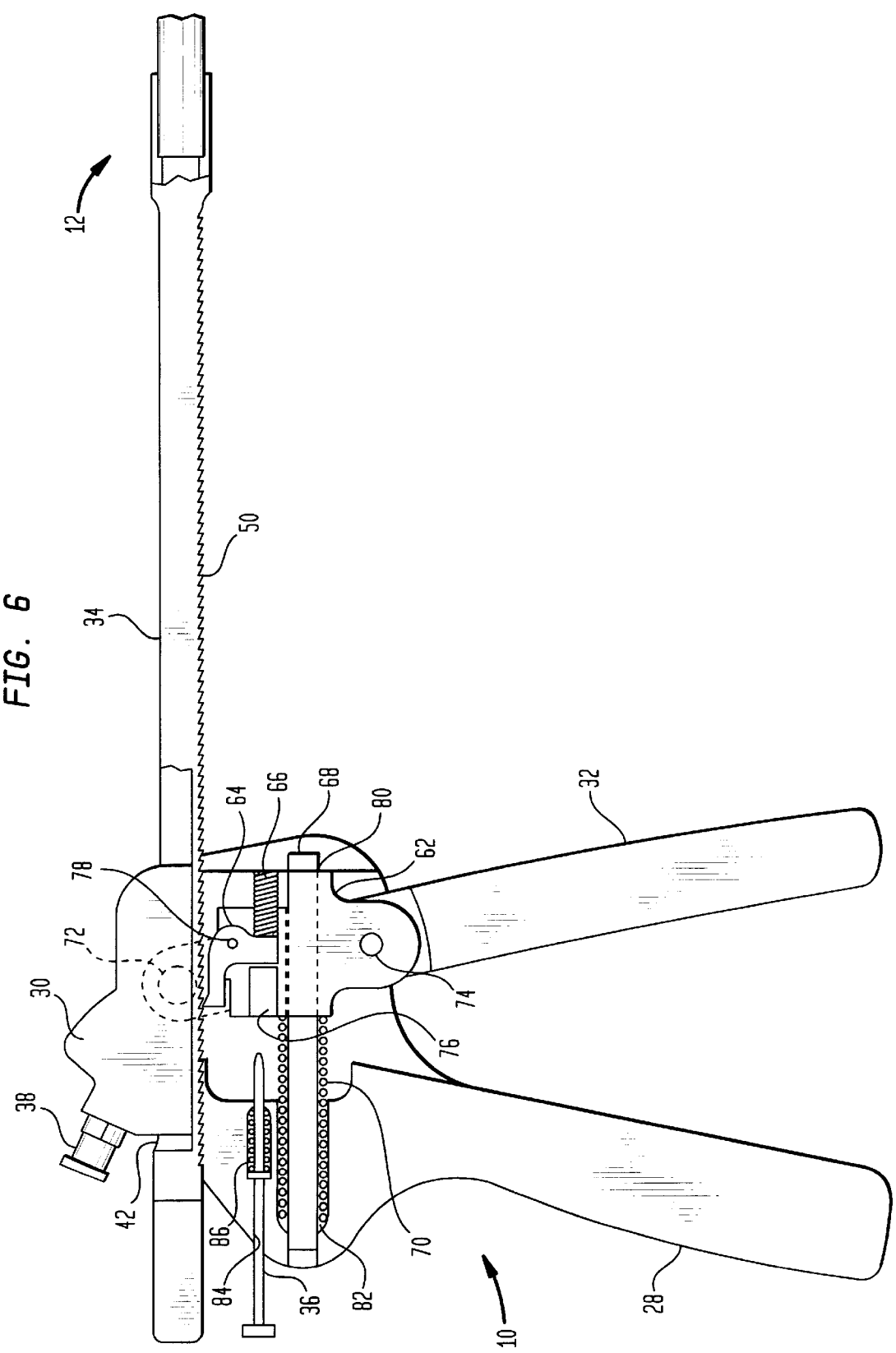
FIG. 6 is an elevation view of the handle, with the right housing removed, exposing the slider and pawl mechanisms.

FIG. 6 illustrates a side elevation view of the handle 10, with the right housing 28 removed. The handle 10 is attached to the breakout 30, as illustrated in FIG. 4. The handle 10 further comprises a slider 62, a pawl 64, a pawl spring 66, a slider rod 68 having proximal and distal ends, and a slider spring 70. The top end of the trigger 32 (shown as dotted lines) is rotatably pinned to the left housing 26 by a first pin 72 (also shown as dotted lines). The slider 62 has a top end and a bottom end and is rotatably pinned to the trigger 32, between the top end and the bottom end of the trigger 32, by a second pin 74. The pawl 64 is rotatably pinned by a third pin 78 to the slider 62. The pawl 64 is biased by the pawl spring 66 such that it contacts the grooves 50 on the ratchet tube 34. The slider 62 has a slider rod lumen 80 and a pawl stop 76 and glides on the slider rod 68. The proximal portion of the slider rod 68 is disposed within a slider rod handle lumen 82 in the left housing 26. The proximal end of the slider rod 68 is attached to the left housing 26. The distal end of the slider rod 68 is disposed within the slider rod lumen 80 and is shown as dotted lines. The slider spring 70 is disposed about the slider 62 between the slider 62 and a proximal end of the slider rod handle lumen 82. A longitudinal cross section of the slider spring 70 is illustrated in FIG. 6 for clarity. Said slider spring 70 biases the slider 62, and thus the trigger 32, to an open position, as illustrated in FIG. 6.

Forcing the trigger 32 towards the left housing 26 by squeezing the trigger 32 and the housing 25 towards each other, pivots the trigger 32 about the first pin 72, and via contact with the second pin 74, slides the slider 62 proximally (or as illustrated in FIG. 6, to the left). As the slider 62 slides on the slider rod 68 proximally, the pawl 64 forces the ratchet tube 34 to move proximally. The distance the ratchet tube 34 travels upon one complete squeezing of the trigger 32 will depend on the geometries of each individual part. Upon release of the trigger 32, the slider spring 70 forces the slider 62 and the trigger 32 back to the position illustrated in FIG. 6. As the slider 62 slides distally, the pawl 64 will follow the contours of the ratchet grooves 50 without moving the ratchet tube 34. Thus, squeezing the trigger 32 results in a proximal movement of the ratchet tube, and ultimately, in a retraction of the sheath 14 relative to the plunger 18. The plunger 18 does not move when the trigger 32 is squeezed because the proximal end of the plunger 18 is attached to the breakout 30 which is attached to the housing 25.

The pawl 64 can be disengaged by pressing a proximal end of the release button 36. The release button 36 is slidingly disposed within a release button lumen 84 in the left housing 26 and is biased in a non-release position, as illustrated in FIG. 6, by a release button spring 86. A longitudinal cross section of the release button spring 86 is shown for clarity. Pressing the proximal end of the release button 36 forces a distal end of the release button 36 to contact the pawl 64 and compress the pawl spring 66. The release button 36 rotates the pawl 64 counterclockwise, and thereby, disengages the pawl 64 from the ratchet grooves 50. Upon removal of the ratchet tube 34 from the handle 10, clockwise rotation of the pawl 64 due to the pawl spring 66 is stopped by the pawl stop 76.

Figure 7:
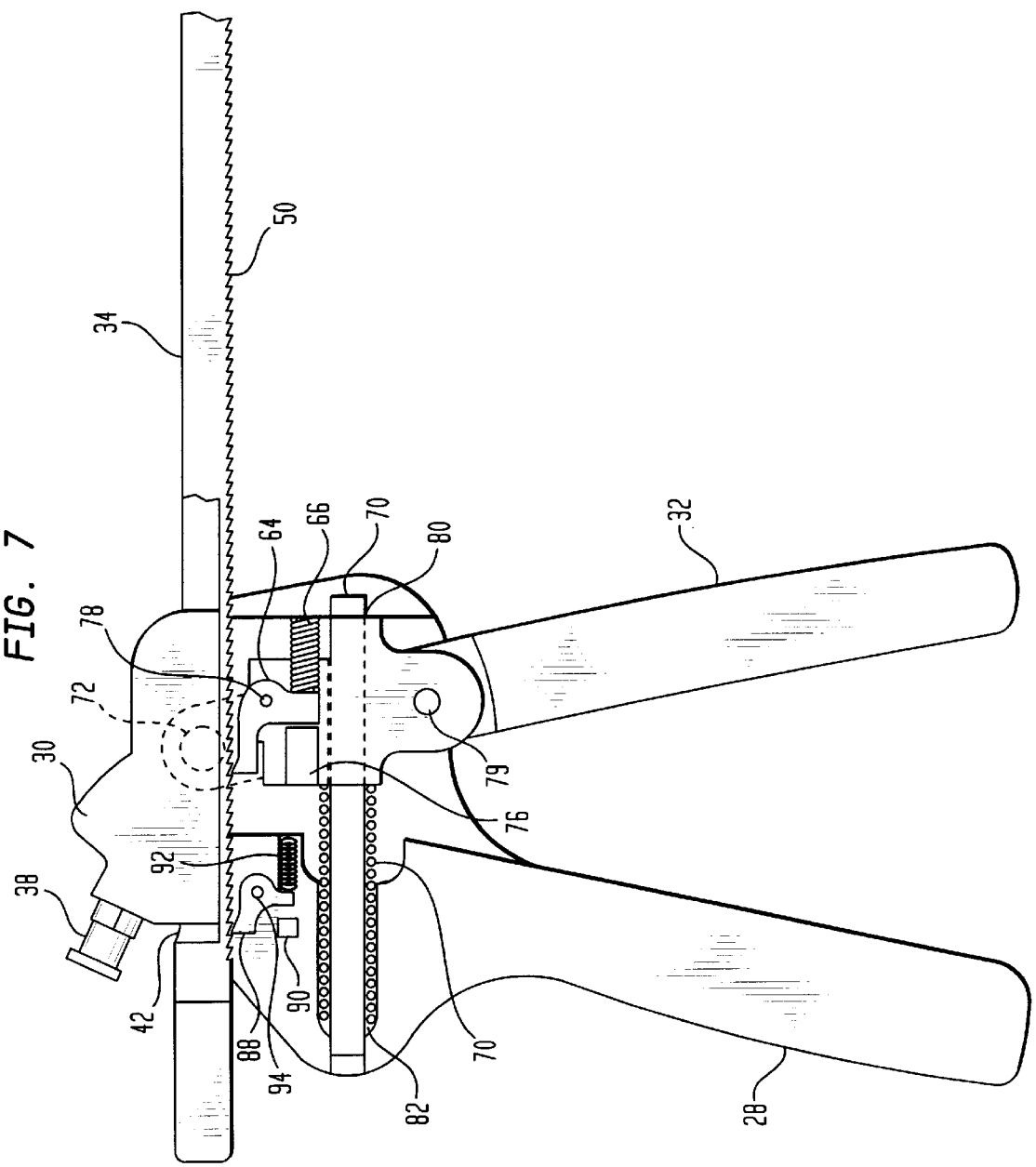
FIG. 7 is an elevation view of an alternate embodiment of the handle having a locking pawl.

An alternate embodiment of the handle 10, as illustrated in FIG. 7, further comprises a locking pawl 88, a locking pawl stop 90, and a locking pawl spring 92. The handle 10 is shown without a release button 36 for clarity. The locking pawl 88 is pivotally connected to the handle 10 by means of a fourth pin 94 and operates in relation to the locking pawl spring 92 and locking pawl stop 90 in the same manner as described for the pawl 64. Note that the locking pawl 88 may also be connected to the handle 10 on the other side, i.e. the distal or right side, of the pawl 64. The sole purpose of the locking pawl 88 is to lock the ratchet tube 34 in place after any proximal movement, caused by squeezing the trigger 32, occurs. The purpose of the pawl 64 is to shift the ratchet tube 34 proximally (as illustrated, to the left), upon squeezing of the trigger 32, and also to lock the ratchet tube 34 in place after release of the trigger 32. The locking pawl 88 may be necessary if the catheter 12 encounters a proximal (towards the heart of the patient) restoring force on it, after the trigger 32 is squeezed, attempting to restore the sheath 14 to its original position. Such a restoring force may result if the sheath 14 is caught on an obstruction in the vasculature of the patient. The necessity of the locking pawl 88 can be realized if one considers what would happen to the ratchet tube 34, as illustrated in FIG. 6, if while squeezing the trigger 32 one also pulls proximally (towards the heart of the patient) on the distal end of the ratchet tube 34. The ratchet tube 34 would shift distally (away from the heart of the patient) as the trigger 32 is squeezed but will shift back proximally upon release of the trigger 32. In such a situation, the locking pawl 88 (FIG. 7) would engage the ratchet tube 34 as soon as the trigger 32 is squeezed and would prevent any proximal movement upon release of the trigger 32. Upon release of the trigger 32, the ratchet tube 34 would stay still but the pawl 64 would shift proximally (towards the heart of the patient) along with the slider 62 and the trigger 32 would be ready to be squeezed again.

What is claimed is:

1. A delivery catheter handle comprising a housing, a trigger pivotally attached to said housing, and a shifting means connected to said housing, a plunger of a delivery catheter is attached to the housing, forces applied to the trigger and the housing in generally opposing directions triggers the shifting means which shifts a sheath of the delivery catheter relative to the fixed plunger.

2. A delivery catheter handle comprising a housing, a trigger having a top end and a bottom, and a shifting means connected to said housing, a plunger of a delivery catheter is attached to the housing, the top end of the trigger is pivotally connected to the housing, the shifting means is actuated by moving the bottom end of the trigger towards the housing, upon actuation the shifting means shifts a sheath of the delivery catheter, the shifting means is actuated when the trigger is squeezed towards the handle.

3. The delivery catheter handle as claimed in claim 2 wherein the shifting means comprises a pawl mechanism pivotally attached to the top end of the trigger.

4. The delivery catheter handle as claimed in claim 2 wherein the shifting means comprises a slider having a top end and a bottom end, a pawl, and a slider rod having a proximal end and a distal end, the bottom end of the slider is pivotally attached to the trigger at a first point between the top end and the bottom end of the trigger, the pawl is pivotally attached to the slider between the first point and the top end of the slider, the slider has a slider lumen, a distal portion of the slider rod is slidingly disposed within the slider lumen in the slider, the proximal end of the slider rod is attached to the housing.

5. The delivery catheter handle as claimed in claim 2 wherein the shifting means comprises a slider having a top end and a bottom end, a pawl, and a slider rod having a proximal end and a distal end, the bottom end of the slider is pivotally attached to the trigger at a first point between the top end and the bottom end of the trigger, the pawl is pivotally attached to the slider between the first point and the top end of the slider, the slider has a slider lumen, a distal portion of the slider rod is slidingly disposed within the slider lumen in the slider, the proximal end of the slider rod is attached to the housing, the pawl engages grooves on an outer surface of the sheath of the delivery catheter and is biased by a pawl spring against said outer surface, a slider spring is disposed about a proximal portion of the slider and biases the trigger away from the housing.

6. The delivery catheter handle as claimed in claim 2 wherein the shifting means comprises a slider having a top end and a bottom end, a pawl, and a slider rod having a proximal end and a distal end, the bottom end of the slider is pivotally attached to the trigger at a first point between the top end and the bottom end of the trigger, the pawl is pivotally attached to the slider between the first point and the top end of the slider, the slider has a slider lumen, a distal portion of the slider rod is slidingly disposed within the slider lumen in the slider, the proximal end of the slider rod is attached to the housing, the pawl engages grooves on an outer surface of a ratchet tube and is biased by a pawl spring against said outer surface, a slider spring is disposed about a proximal portion of the slider and biases the slider and the trigger away from the housing, the ratchet tube has a proximal end, a distal end, and a longitudinal ratchet tube slot, the distal end of the ratchet tube is attached to the sheath, a proximal portion of the plunger is disposed within the ratchet tube.

7. The delivery catheter handle as claimed in claim 2 wherein the shifting means comprises a slider having a top end and a bottom end, a pawl, and a slider rod having a proximal end and a distal end, the bottom end of the slider is pivotally attached to the trigger at a first point between the top end and the bottom end of the trigger, the pawl is pivotally attached to the slider between the first point and the top end of the slider, the slider has a slider lumen, a distal portion of the slider rod is slidingly disposed within the slider lumen in the slider, the proximal end of the slider rod is attached to the housing, the pawl engages grooves on an outer surface of a ratchet tube and is biased by a pawl spring against said outer surface, a slider spring is disposed about a proximal portion of the slider and biases the trigger away from the housing, the ratchet tube has a proximal end, a distal end, and a longitudinal ratchet tube slot, the distal end of the ratchet tube is attached to the sheath, a proximal portion of the plunger is disposed within the ratchet tube, a proximal end of the plunger is attached to a breakout, the breakout is removably attached to the housing and slides within the ratchet tube slot.

8. A delivery catheter handle comprising a housing, a trigger having a top end and a bottom end, and a shifting means connected to the housing, the top end of the trigger is pivotally attached to the housing, the shifting means is actuated by moving the bottom end of the trigger towards the housing, upon actuation the shifting means shifts a sheath of a delivery catheter towards the handle, the shifting means is actuated when the trigger is squeezed towards the handle, the shifting means comprises a slider having a top end and a bottom end, a pawl pivotally connected to the slider, and a slider rod having a proximal end and a distal end, the bottom end of the slider is pivotally attached to the trigger at a first point between the top end and the bottom end of the trigger, the pawl is pivotally connected to the slider between the first point and the top end of the slider, the slider has a slider lumen, a distal portion of the slider rod is slidingly disposed within said slider lumen, the proximal end of the slider rod is connected to the housing, the pawl engages grooves on an outer surface of a ratchet tube and is biased by a pawl spring connected to the slider against said outer surface, a slider spring is disposed about a proximal portion of the slider and biases the trigger away from the housing, the ratchet tube has a proximal end, a distal end, and a longitudinal ratchet tube slot, the distal end of the ratchet tube is attached to the sheath, a proximal portion of a plunger of the delivery catheter is disposed within the ratchet tube, a proximal end of the plunger is attached to a breakout, the breakout is removably attached to the housing and slides within the ratchet tube slot.

9. The delivery catheter as claimed in claim 8 further comprising a release pin slidingly disposed in a release pin lumen in the housing, contact of a distal end of the release pin with the pawl disengages the pawl from the grooves on the outer surface of the ratchet tube.

10. The delivery catheter as claimed in claim 8 wherein the breakout further comprises a proximal end, a distal end, a pair of longitudinal opposing slots on both sides of the proximal end of the breakout, and a pair of opposing holes on both sides of the distal end of the breakout, and the handle further comprises a breakout slot having a proximal end and a distal end, a pair of opposing fist pins attached to the handle which project into the proximal end of said breakout slot, and a single second pin attached to the handle which projects into the distal end of the breakout slot, the opposing first pins fit into the opposing slots on both sides of the proximal end of the breakout, the second pin fits into one of the holes on the distal end of the breakout, the handle has a hole directly facing the holes in the distal end of the breakout, a securing device occupies the hole in the handle and one of the unoccupied holes in the distal end of the breakout and secures the breakout to the handle.

\* \* \* \* \*